(12) United States Patent
Halter et al.

(10) Patent No.: US 11,304,688 B2
(45) Date of Patent: Apr. 19, 2022

(54) GASTROCUTANEOUS CLOSURE DEVICE

(71) Applicant: Maine Medical Center, Portland, ME (US)

(72) Inventors: Jeffrey M. Halter, Cape Elizabeth, ME (US); Chad P. Seeley, Gorham, ME (US); Asheesh Ravikumar Lanba, Gorham, ME (US)

(73) Assignees: Maine Medical Center, Portland, ME (US); University of Southern Maine, Portland, ME (US)

( * ) Notice: Subject to any disclaimer, the term of this patent is extended or adjusted under 35 U.S.C. 154(b) by 140 days.

(21) Appl. No.: 16/893,380

(22) Filed: Jun. 4, 2020

(65) Prior Publication Data
US 2020/0383667 A1 Dec. 10, 2020

Related U.S. Application Data

(60) Provisional application No. 62/857,351, filed on Jun. 5, 2019.

(51) Int. Cl.
*A61B 17/00* (2006.01)
*A61B 18/06* (2006.01)
(Continued)

(52) U.S. Cl.
CPC .......... *A61B 17/0057* (2013.01); *A61B 18/06* (2013.01); *A61K 33/38* (2013.01);
(Continued)

(58) Field of Classification Search
CPC ................ A61B 17/0057; A61B 18/06; A61B 2017/00584; A61B 2017/0061;
(Continued)

(56) References Cited

U.S. PATENT DOCUMENTS 6,517,556 B1 2/2003 Monassevitch
6,695,867 B2 2/2004 Ginn et al.
(Continued)

FOREIGN PATENT DOCUMENTS

CN 103874466 A 6/2014
WO 2018075707 A1 4/2018

OTHER PUBLICATIONS

International Search Report, PCT/US2020/036206, pp. 2, dated Oct. 12, 2020.

*Primary Examiner* — George J Ulsh
*Assistant Examiner* — David P Stein
(74) *Attorney, Agent, or Firm* — Armis IP Law, LLC

(57) ABSTRACT

A gastrocutaneous closure device allows gastrocutaneous fistula closure from external abdominal access through the fistula site. Access through the fistula ensures accurate closure placement on the interior lumen wall of the stomach. A closure or clip has a plurality of prongs defined by a deformable material, such that the prongs extend radially from a central hub in an arcuate or curved, semicircular shape. The arcuate shape converges towards a central point or axis at a distal end, and the proximate end of the prongs attaches to the central hub such that the prongs radiate from the hub and the distal end curves back toward the axis through the hub. The deformable prongs may therefore radially compress or retract to define a larger or smaller diameter. The fistula lies on the axis such that the biased, inserted prongs pull the inner stomach wall closed around the healing fistula.

20 Claims, 15 Drawing Sheets

(51) Int. Cl.
*A61K 33/38* (2006.01)
*A61B 18/00* (2006.01)

(52) U.S. Cl.
CPC .............. *A61B 2017/0061* (2013.01); *A61B 2017/00584* (2013.01); *A61B 2017/00623* (2013.01); *A61B 2017/00637* (2013.01); *A61B 2017/00818* (2013.01); *A61B 2018/00494* (2013.01); *A61B 2018/00595* (2013.01)

(58) Field of Classification Search
CPC ........... A61B 2017/00623; A61B 2017/00637; A61B 2017/00818; A61B 2018/00494; A61B 2018/00595; A61K 33/38
See application file for complete search history.

(56) References Cited

U.S. PATENT DOCUMENTS

| | | |
|---|---|---|
| 7,744,610 B2 | 6/2010 | Hausen |
| 8,007,512 B2 | 8/2011 | Ginn et al. |
| 8,048,108 B2 | 11/2011 | Sibbitt, Jr. et al. |
| 8,192,461 B2 | 6/2012 | Kochman et al. |
| 8,480,687 B2 | 7/2013 | Ducharme et al. |
| 8,758,397 B2 | 6/2014 | Sibbitt, Jr. et al. |
| 8,920,442 B2 | 12/2014 | Sibbitt, Jr. et al. |
| 8,926,576 B2 | 1/2015 | Mikkaichi |
| 9,050,066 B2 | 6/2015 | Lichtenstein |
| 9,072,517 B2 | 7/2015 | Qadeer |
| 9,168,041 B2 | 10/2015 | Zaritsky et al. |
| 9,295,463 B2 | 3/2016 | Viola et al. |
| 9,301,754 B2 | 4/2016 | Duncan |
| 9,320,522 B2 | 4/2016 | Carley et al. |
| 9,414,822 B2 | 8/2016 | Ziobro et al. |
| 9,463,019 B2 | 10/2016 | Metzinger |
| 9,848,879 B2 | 12/2017 | Prior et al. |
| 9,848,884 B2 | 12/2017 | Bertollo et al. |
| 9,861,364 B2 | 1/2018 | Prior et al. |
| 9,918,706 B2 | 3/2018 | Lichtenstein |
| 10,028,733 B2 | 7/2018 | Bambury et al. |
| 10,052,105 B2 | 8/2018 | Tannhauser et al. |
| 10,123,789 B1 | 11/2018 | Kennedy et al. |
| 10,130,365 B2 | 11/2018 | Hotter |
| 10,201,339 B2 | 2/2019 | Raybin et al. |
| 2010/0076463 A1 | 3/2010 | Mavani et al. |
| 2017/0311937 A1 | 11/2017 | Bambury et al. |

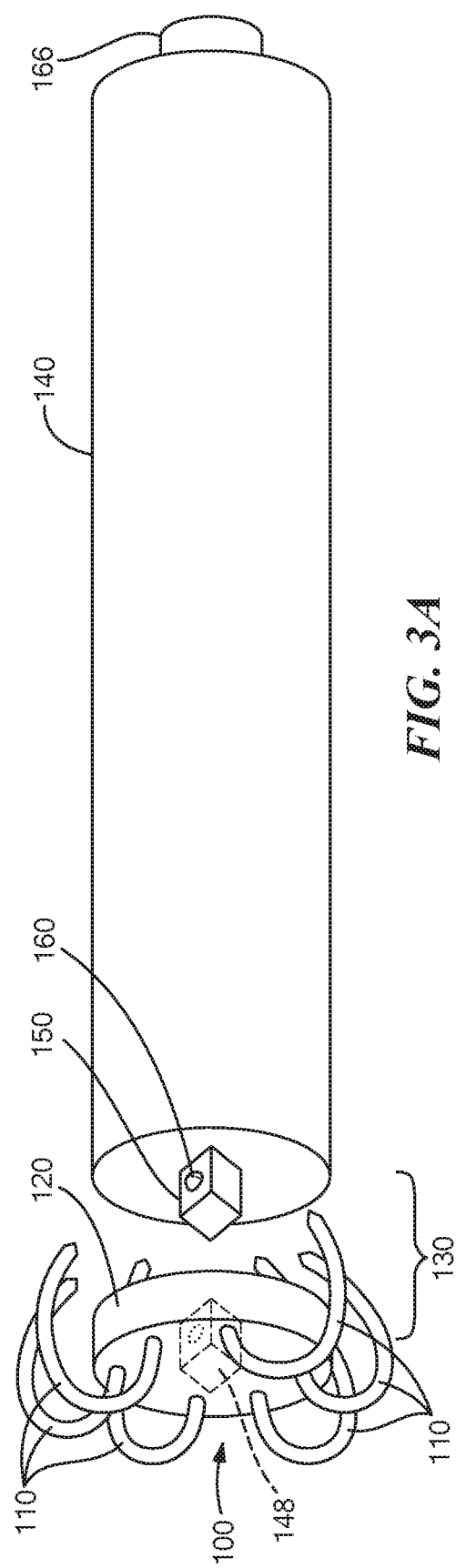
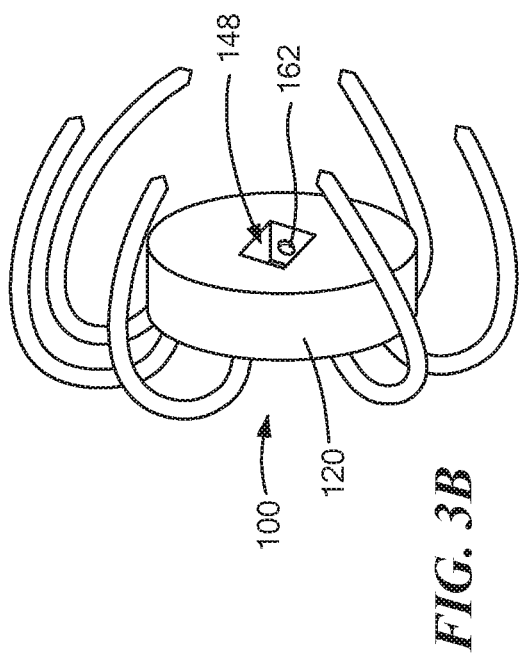
FIG. 3A
FIG. 3B

GASTROCUTANEOUS CLOSURE DEVICE

RELATED APPLICATIONS

This patent application claims the benefit under 35 U.S.C. § 119(e) of U.S. Provisional Patent App. No. 62/857,351, filed Jun. 5, 2019, entitled "GASTROCUTANEOUS CLOSURE DEVICE," incorporated herein by reference in entirety.

BACKGROUND

Gastrostomy tubes provide an effective fluid conduit for medicinal and/or food administration to patients unresponsive to oral administration. A gastrocutaneous fistula results from a surgical orifice through epidermal, muscle and stomach tissue for inserting the gastrostomy tube directly into the stomach lumen.

Following treatment, gastrostomy tube removal often requires surgical intervention to effectively close the gastrocutaneous (gastro) fistula. Although some fistulas close naturally, similar to an unused body piercing, a surgical closure is required in approximately half the cases, thus increasing medical costs. An evaluation of the gastro site about 3 weeks following tube removal validates whether surgical closure is necessary, typically because highly acidic stomach fluids expelled though the fistula exacerbate the fistula site.

Endoscopic treatments for accessing the interior stomach wall through the esophagus can be complicated by the need to accurately target the fistula site from within the stomach lumen. Visibility and uneven tissue surface can cause a conventional so-called "padlock closure" to misalign with the fistula opening.

SUMMARY

A gastrocutaneous closure device allows gastrocutaneous fistula closure from external abdominal access through the fistula site. Access through the fistula ensures accurate closure placement on the interior lumen wall of the stomach. A closure or clip has a plurality of prongs defined by a deformable material, such that the prongs extend radially from a central hub in an arcuate or curved, semicircular shape. The arcuate shape converges towards a central point or axis at a distal end, and the proximate end of the prongs attaches to the central hub such that the prongs radiate from the hub and the distal end curves back toward the axis through the hub. The deformable prongs may therefore radially compress or retract to define a larger or smaller diameter.

An elongated shaft is adapted to selectively engage the central hub of the clip for implantation. The elongated shaft has a length based on a gastric tract resulting from the g-tube (gastrostomy tube) removal to allow for manual insertion to a depth into the stomach lumen. A sleeve has a diameter for insertion into a surgical tract defining the gastrocutaneous fistula for the recently removed g-tube, such that an inside diameter of the sleeve compresses the clip for passage of the shaft.

The clip is adapted to attach to an insertable end of the shaft and to radially compress for slidable passage through the sleeve for insertion into a stomach lumen. The sleeve walls compress and draw the distal ends, or tips, of the prongs towards the central axis now defined by the shaft. Upon insertion through the gastrocutaneous fistula into the stomach interior, the clip is pushed out the end of the shaft to return to a rest or undeformed position inside the stomach lumen. The shaft then partially retracts to force the clip against the sleeve, which in turn radially expands the prongs in response to partial retraction of the shaft through the sleeve. The undeformed clip has a diameter larger than the sleeve, such that once pushed through the sleeve, it expands to a radial diameter greater than the sleeve. The prongs are now on the outside of the sleeve and expand further as the sleeve is disposed against the prongs near the proximate (hub) end.

The sleeve and shaft are retracted together to dispose the clip against the interior stomach wall, and the sleeve withdrawn to allow the clip to radially compress against the interior stomach wall for engaging the prongs against the stomach wall and drawing the stomach wall inward toward the hub for closing the fistula.

The clip typically between 4 and 6 prongs and is adapted to radially compress to a compressed diameter for sleeve insertion and radially expand to an expanded diameter for engaging the interior stomach wall prior to fistula closure, however any suitable number of prongs may be employed.

In particular configurations, the sleeve is configured to retain a cauterization substance such as silver nitrate for deposition or release around the gastrocutaneous fistula during insertion. Alternatively, the cauterization substance may be directly applied to the fistula site to promote healing.

More specifically, a configuration of the gastrocutaneous clip device discussed further below includes a plurality of prongs defined by a deformable material. The prongs extend radially from a forward side of a central hub in an inverted shape, having a generally arced, "U" or semicircular shape, such that the inverted shape of each of the prongs converges towards a central point at a distal end. A linkage on a rearward side of the central hub is adapted for selective engagement with an insertion shaft for insertion and release of the central hub. The prongs extend in a forward or lateral direction from the central hub, in which the forward direction is opposed from the rearward side, and invert towards facing a rearward direction defined by the rearward side at the distal end. A surgical tip at the distal end of each prong is adapted for engaging a surgical region in a converging, circular manner as each prong is adapted to deformably articulate for disposing the plurality of prongs in a radial arrangement around a closure site defined by the gastric fistula.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 3A-3B show a linkage and selective detachment of the clip and insertion shaft;

DETAILED DESCRIPTION

Figure 1B:
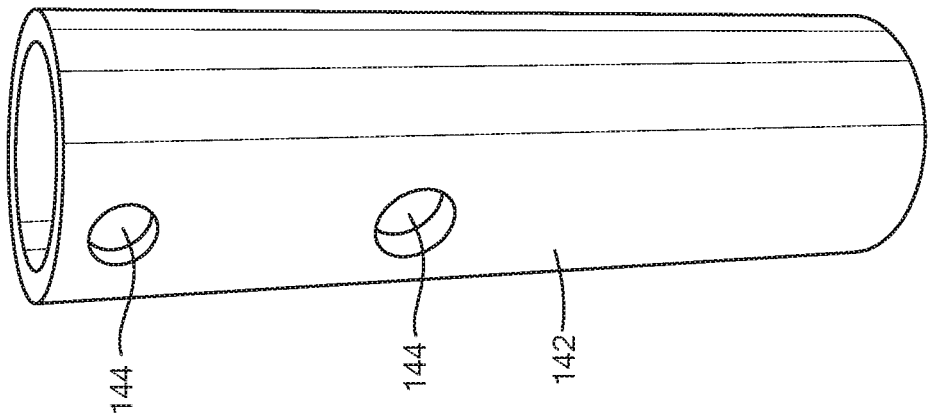
FIGS. 1A-1C show perspective views of a general configuration suitable for practicing the invention disclosed and claimed herein.

Depicted below are several examples of a gastrocutaneous clip for surgical closure of a gastric fistula following gastrostomy tube removal. Gastrostomy tubes (g-tubes), which are surgically placed tubes directly through the abdominal wall into the stomach, are life sustaining for many patients for both medications and nutrition. There are currently almost half a million g-tube patients in the US alone. Fortunately, many patients improve and no longer require the g-tube and are able to have it removed. Current standard practice is simply removal of the tube, either at home by the patient or parent, or by the clinician in the office, and then watchful waiting for the site to heal shut, typically 3 to 6 weeks. However, a persistent gastrocutaneous fistula (GCF) tract may occur after the g-tube is removed, much like a pierced earring maintains a hole after removal. This can occur in up to 40% of these sites after g-tube removal. This results in leakage of stomach contents and acid, irritation or ulceration of the skin, avoidance of food intake to minimize the leakage resulting in malnutrition, and ultimately requires surgical closure after weeks of failure and patient suffering. This also mandates anesthesia for surgical or endoscopic closure, with the associated risks, expense, and inconvenience. With some institutional variability, the typical cost for surgical or endoscopic closure has been estimated between $8,000 and $12,000.

In a particular configuration, the gastrocutaneous clip is particularly amenable for closure of the gastrocutaneous fistula at the time of tube removal in the clinician's office. Removal is routine and only requires deflating of a balloon holding the tube in place. After removal, the device would be inserted through the g-tube site to achieve 2 objectives: 1) Chemical cauterization of the tract to remove the lining to promote healing, and 2) Deploy the clip device on the interior of the stomach. With obstruction of the caustic gastric leakage and removal of the lining of the tract, the site is optimized for healing, and can all be done without anesthesia in about 5 minutes. There are a several properties of the clip itself: it is preferably 4- or 6-pronged, and should be sufficiently deformable to allow it to fit through the existing g-tube site, and have enough memory to provide sufficient closure, such as nitinol, an alloy that may also employ a temperature-sensitive shape memory at body temperature. The shaft of the deployment device would be impregnated with silver nitrate, a common chemical cauterization compound.

Conventional endoscopic and/or gastric closure approaches include a so-called "Padlock" ™ system. The padlock system employs a flat, planar member having sharp points in a star-like arrangement. In contrast to the claimed approach, the star shaped padlock device is compressed and retained in an insertion vessel, and allowed to expand once inserted. In contrast, the claimed clip includes is a 3-dimensional structure with deformable prongs slidably compressed during insertion, the prongs deformably expanded, and subsequently contracted for closure of the surgical site.

Figure 1A:
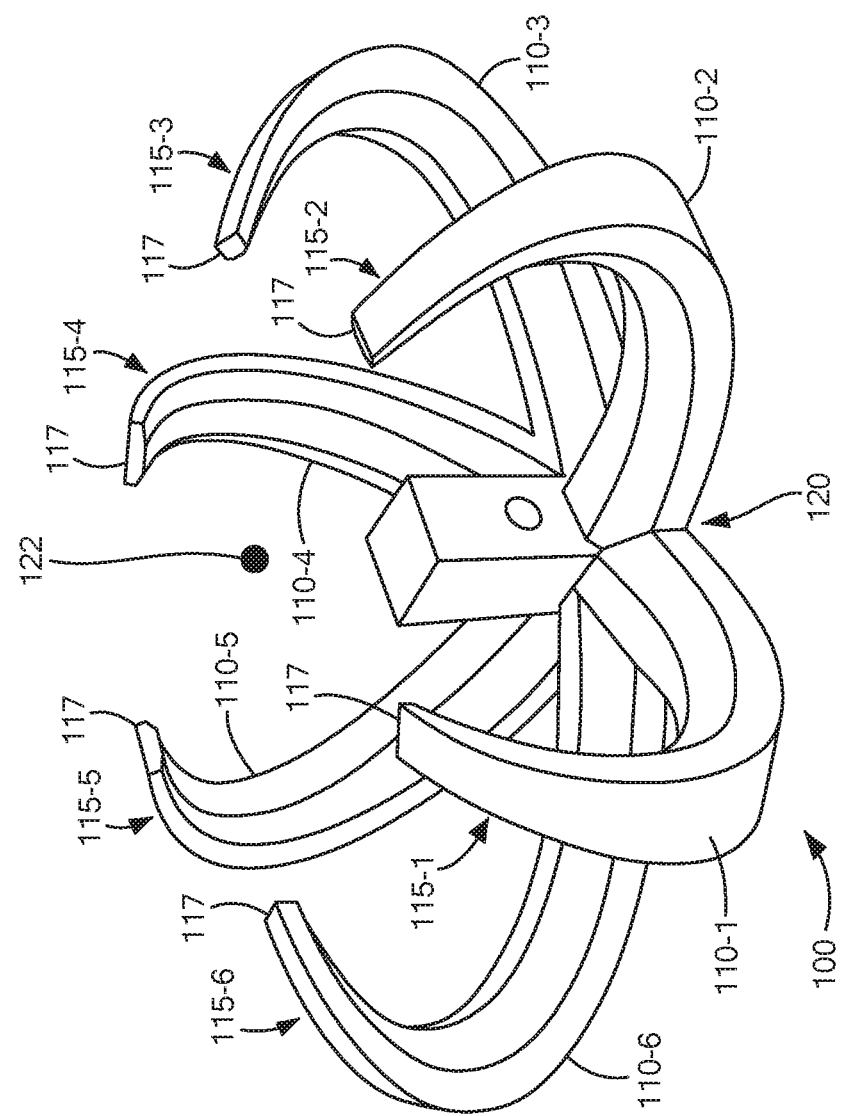
Figure 1C:
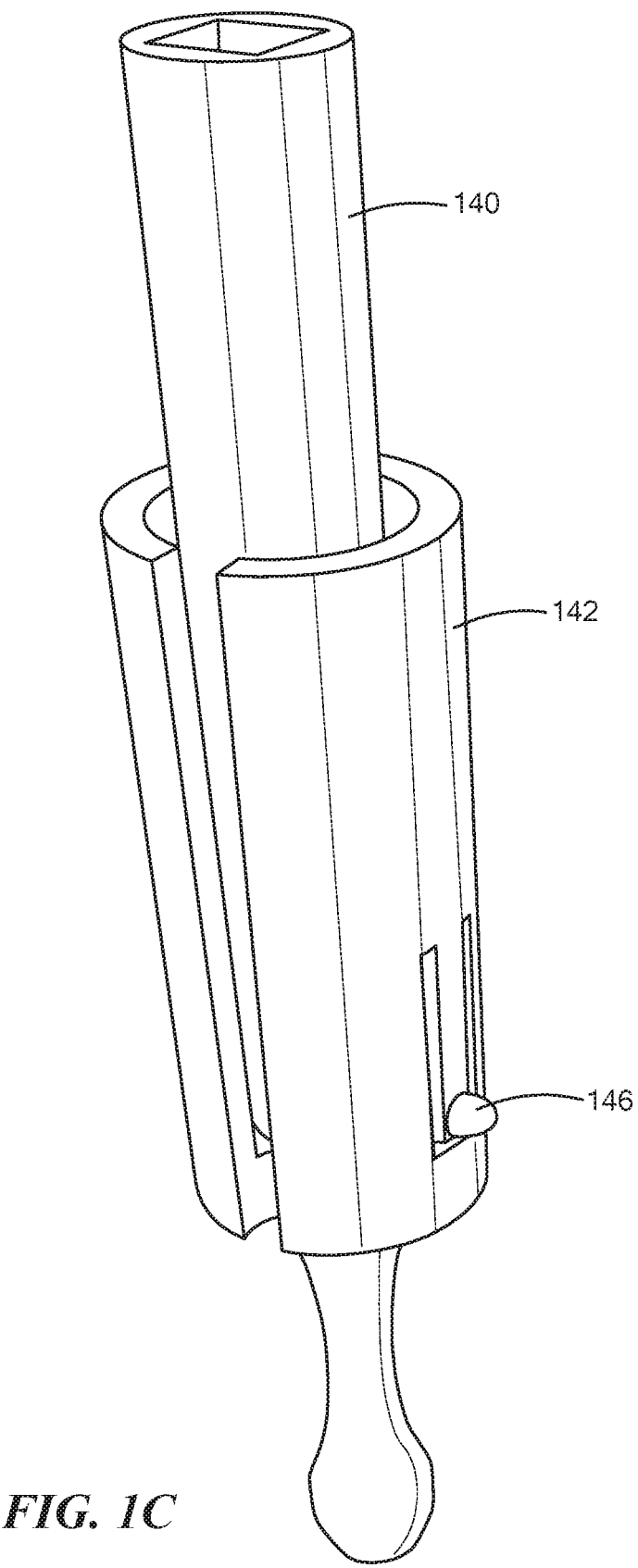

FIGS. 1A-1C show perspective views of a general configuration suitable for practicing the invention disclosed and claimed herein. Referring to FIGS. 1A-1C, the gastrocutaneous clip 100 includes a plurality of prongs 110-1 ... 110-6 (110 generally) defined by a deformable material, the prongs extending radially from a forward or lateral side of a central hub 120 in an inverted shape, such that the inverted shape of each of the plurality of prongs 110 converges towards a central point 122 at a distal end of each prong. A linkage 130 on a rearward side of the central hub 120 is adapted for selectively engaging an insertion shaft 140 for insertion and release of the central hub 120 during clip 100 installation.

The prongs 110 extend in a lateral or forward direction from the central hub 120, such that the forward direction is opposed from the rearward side where a shaft 140 has a socket 148 or receptacle for engaging the linkage 130. The prongs 110 then curve or invert along their length towards a rearward facing direction defined by the rearward side at the distal end 115-1 ... 115-6 (115 generally) of the prongs. A surgical tip 117 at the distal end of each prong of the plurality of prongs 110 has a pointed or piercing shape adapted for engaging a surgical region such as the fistula and closing it from the inside. Each prong 110 is therefore adapted to deformably articulate for disposing the plurality of prongs in a radial arrangement around a closure site, and drawing the surgical tips 117 in a circumferential manner around the fistula for closure.

An insertion sleeve 142 has a diameter for insertion into a surgical tract defining a gastrocutaneous fistula following gastrostomy tube removal, discussed further below. An inside diameter of the sleeve 142 is adapted for passage of the shaft 140 and clip 100. Apertures 144 may serve as depth indicators and stops, and may be in conjunction with dimples 146.

Figure 2A:
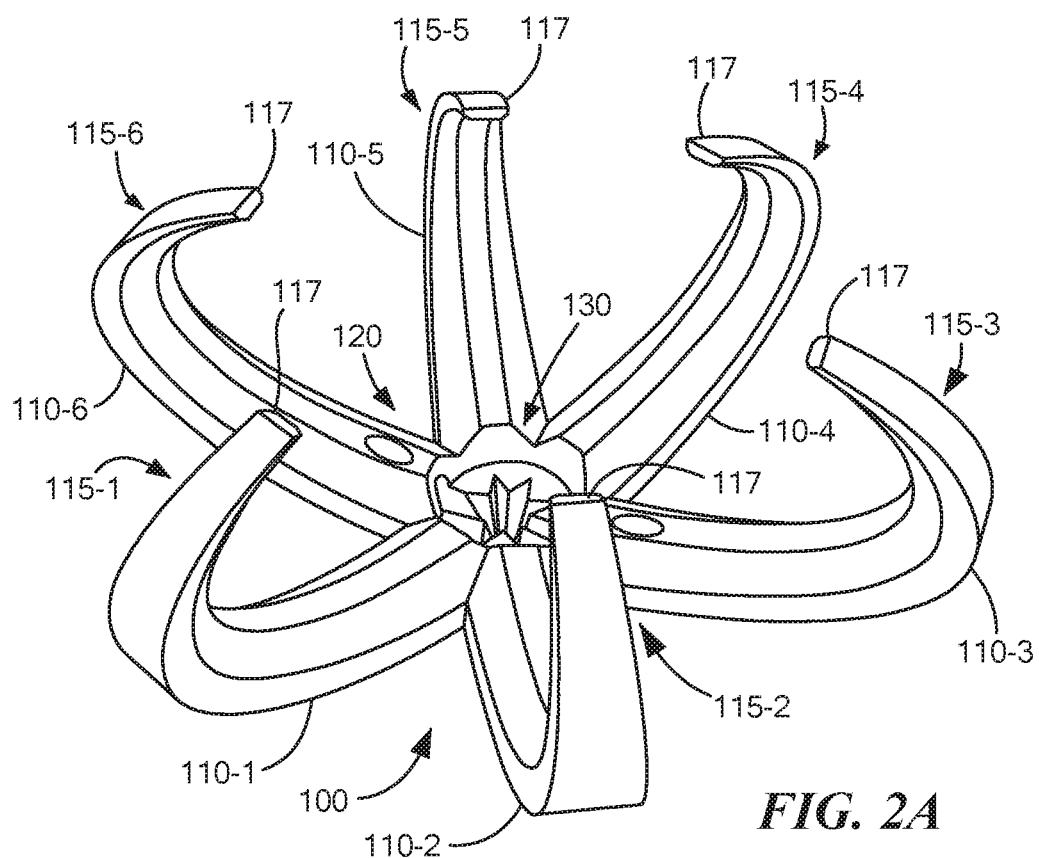
FIGS. 2A-2C show an alternate configuration of the gastrocutaneous clip as defined herein.
Figure 2B:
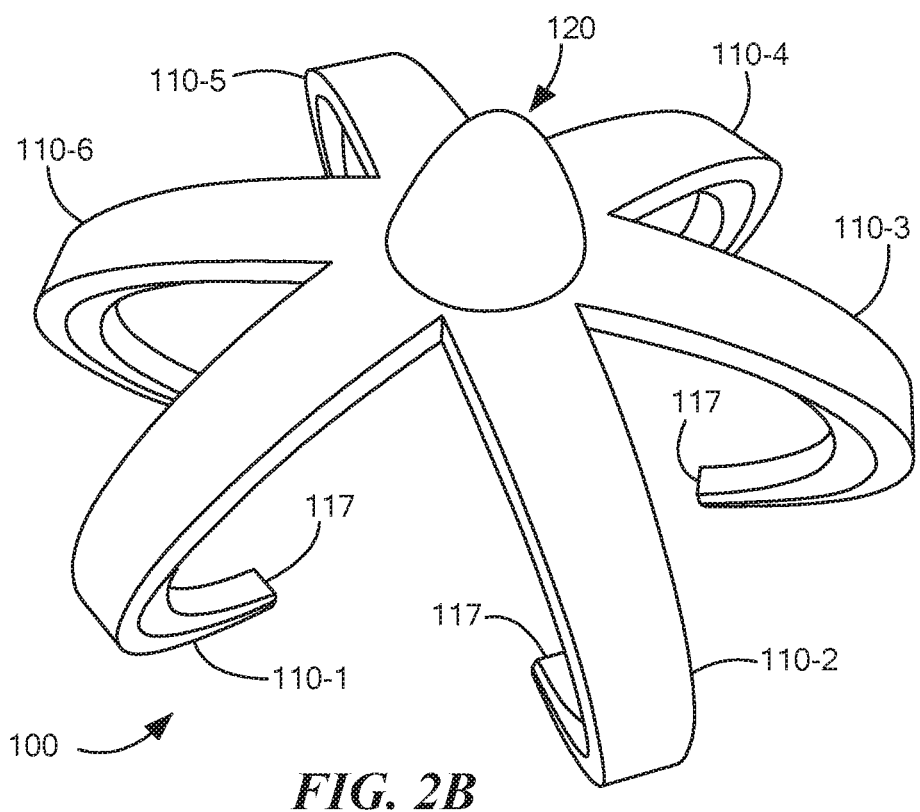
Figure 2C:
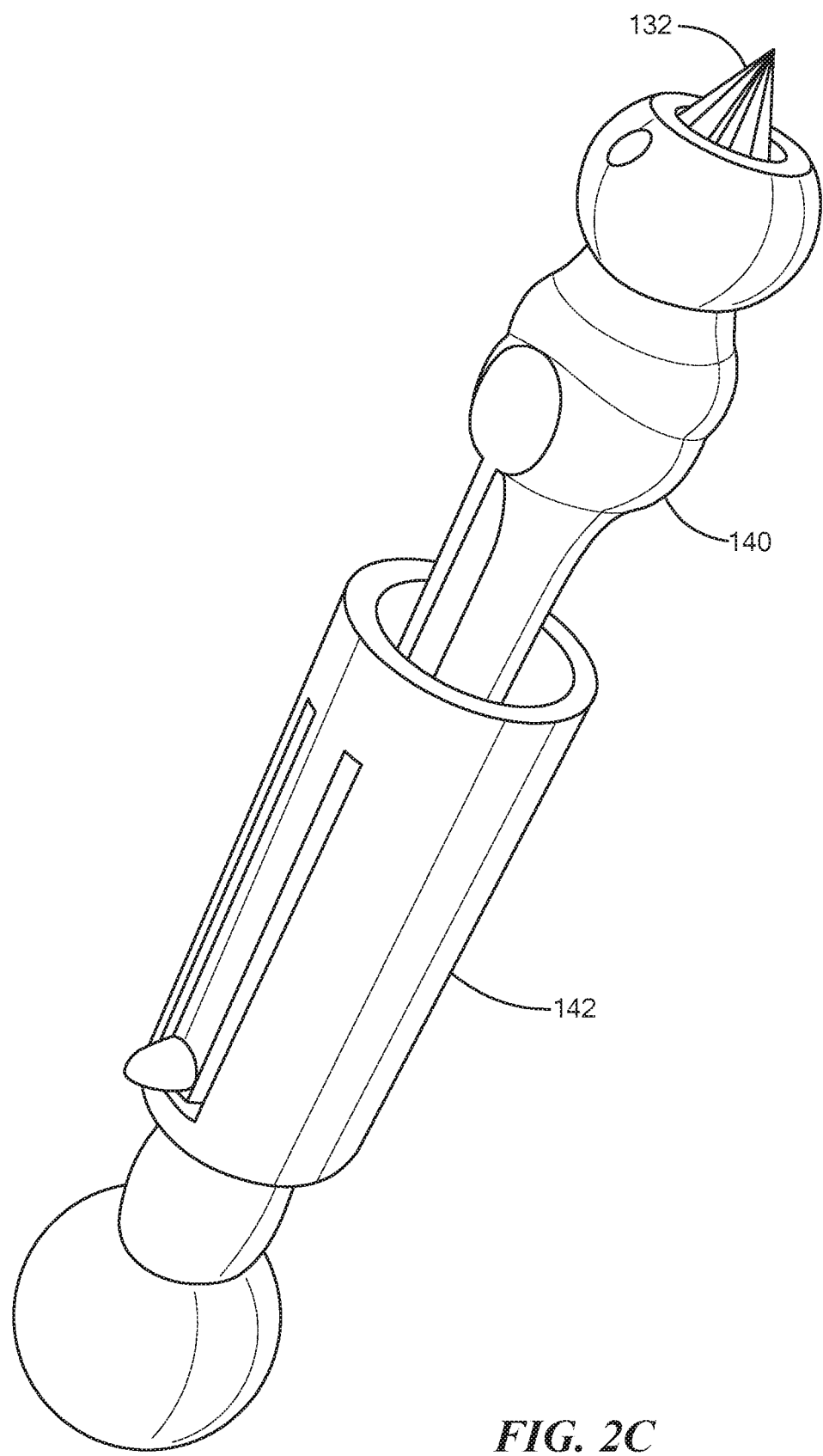

FIGS. 2A-2C show an alternate configuration of the gastrocutaneous clip as defined herein. Referring to FIGS. 2A-2C, the linkage 130 allows disengagement of the clip 130 once inserted into the lumen (cavity) of the stomach for securing the surgical site from the internal side. The linkage 130 attaches the clip 100 until a controlled detachment, and may include a square, circular or polygonal insertion tip on one of the insertion shaft 140 and the central hub 120. A corresponding tip receptacle or socket 148 on the other of the insertion shaft 140 and the central hub 100 defines the linkage 130. A selective retention is also provided by least one protrusion extending perpendicularly from an axis defined by an elongated direction of the insertion shaft, discussed further below in FIGS. 3A-3B.

FIGS. 3A-3B show a linkage and selective detachment of the clip and insertion shaft. Referring to FIGS. 1A-3B, the socket 148 receives a matching engagement member 150 of a corresponding polygonal shape. Similarly, the socket 148 and engagement member 150 (protrusion or appendage) may take either complementary side without departing from the scope of the invention. A retention mechanism may include a ball 160 and dimple 162 arrangement disposed perpendicular to the travel of socket engagement, discussed further below in FIGS. 5A-5B. FIG. 3B shows a perspective of the engagement side of the central hub 120, denoting the socket 148 and dimple 162 for receiving the ball 160 or other protrusion.

FIGS. 4A-4F show an installation of the clip of FIGS. 1A-3B depicting the deformability of the prongs 110. Referring to FIGS. 1A-4F, the deformable prongs 110 of the clip 100 provide a beneficial feature, along with insertion and retraction using the insertion shaft 140, sleeve 142 and linkage 130, to implant the clip in an internal stomach wall or similar surgical structure. In the sequence shown from FIGS. 4A-4F, the clip 100 defines a gastrocutaneous closure device having a plurality of prongs 110, each of a deformable material. The prongs 110 extend radially from the central hub 120 in an arcuate shape for converging towards a central point 122 at a distal end 115 for fistula 200 closure. A proximate end of the prongs attaches to and extends from the central hub 120. The elongated insertion shaft 140 is adapted to selectively engage the central hub 120, in which the elongated shaft 140 has a length based on a gastric tract 210 resulting from a gastrostomy tube removal. The sleeve 142 has a diameter for insertion into the surgical tract 210 defining the gastrocutaneous fistula 200, and an inside diameter of the sleeve 143 is adapted for passage of the shaft 140 and the deformed prongs 110 of the clip 100.

Figure 4A:
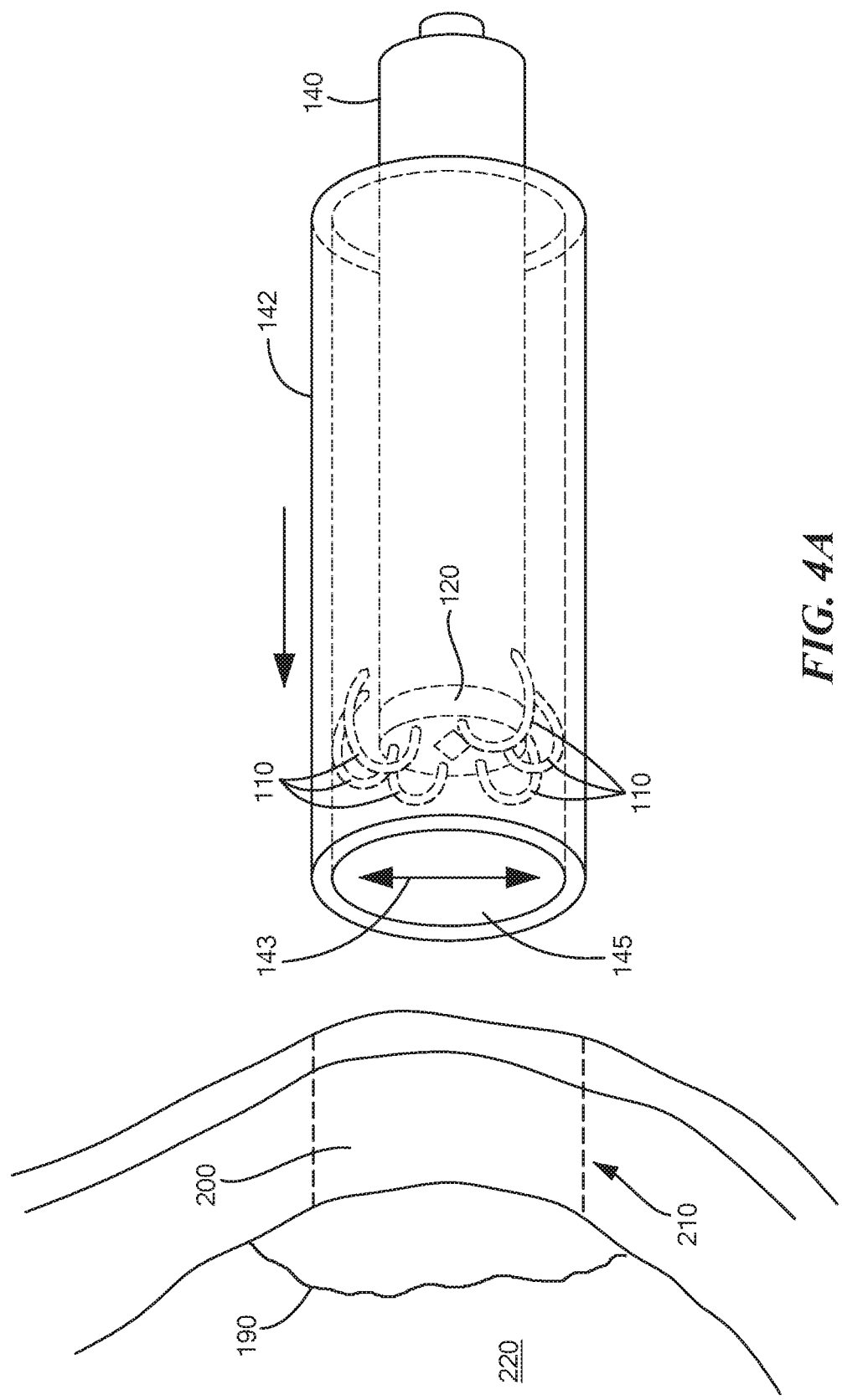
FIGS. 4A-4F show an installation of the clip of FIGS. 1A-3B depicting the deformability of the prongs.
Figure 4B:
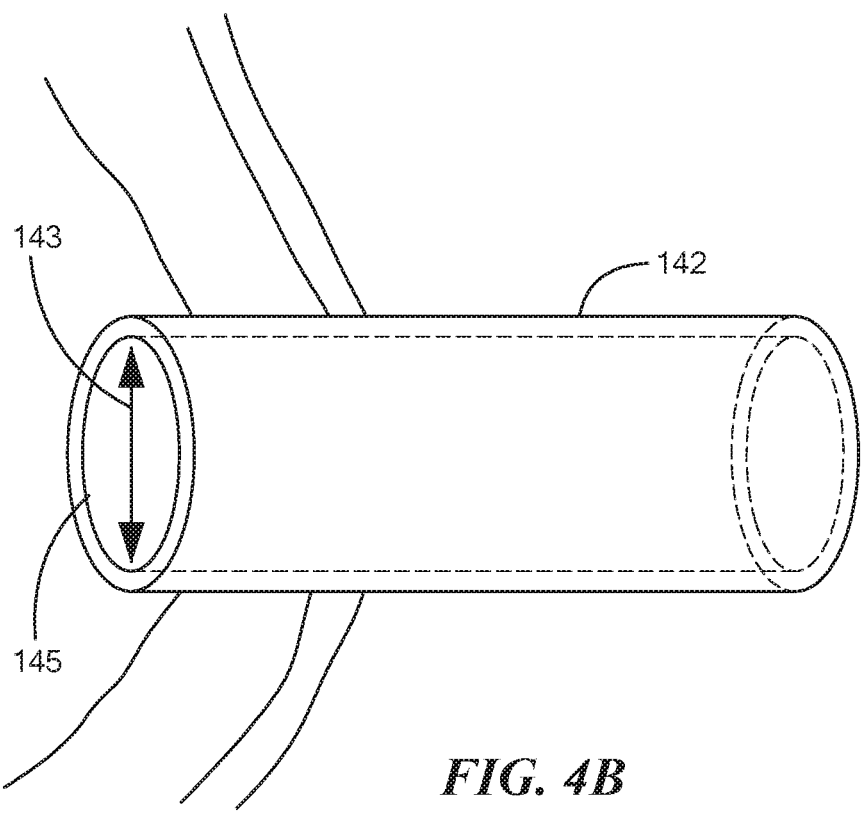
Figure 4C:
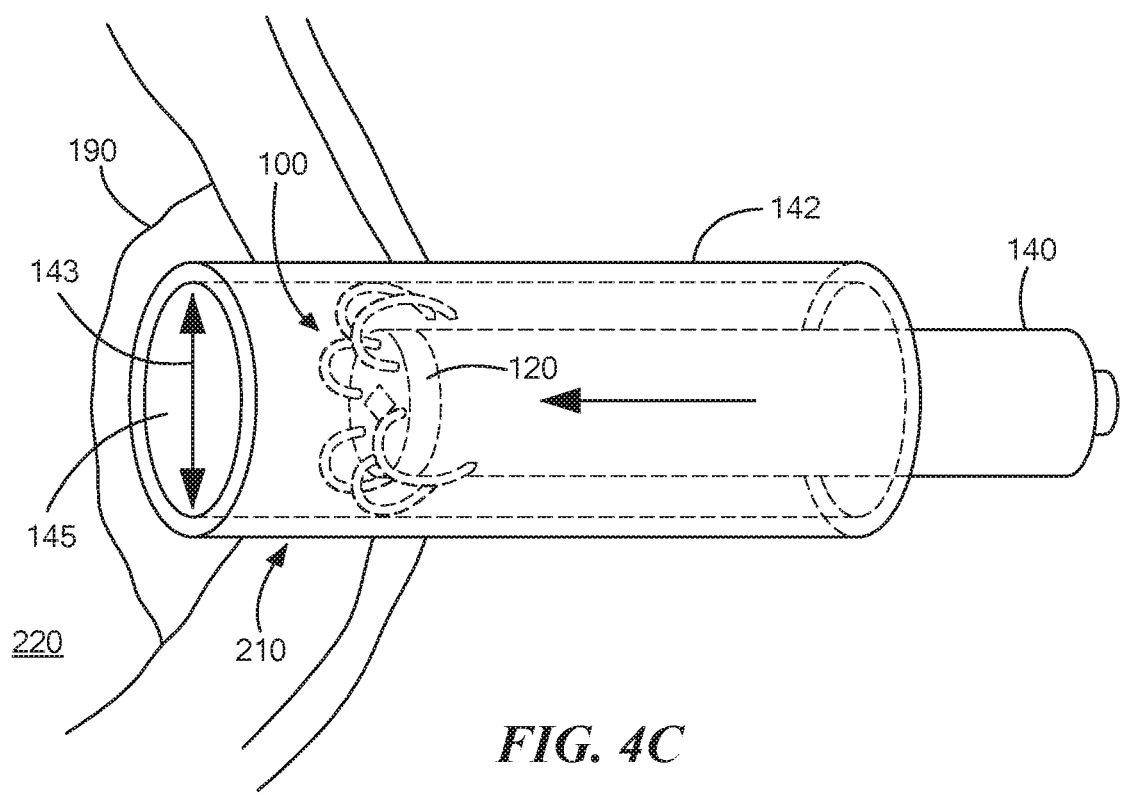

FIG. 4B shows the sleeve 142 inserted through the fistula 200 in the tract 210 in preparation for clip 110 installation. In FIG. 4C, the insertion shaft 140 advances the clip 100 as the plurality of prongs 110 are adapted to slideably engage an inner annular surface 145 of the insertion sleeve 142. Upon insertion into the sleeve 142, the prongs 110 radially compress for passage through the sleeve 142 in preparation for insertion into a stomach lumen 220. The inner annular surface 145 has a diameter 143 based on a compressed articulation of each prong 110 of the plurality of prongs as the central hub 120 disposes axially through the tube 142 for insertion. The sleeve 142 is also configured to retain a cauterization substance such as silver nitrate for deposition or release around the gastrocutaneous fistula during insertion, further assisting healing and mitigating bleeding.

Figure 4D:
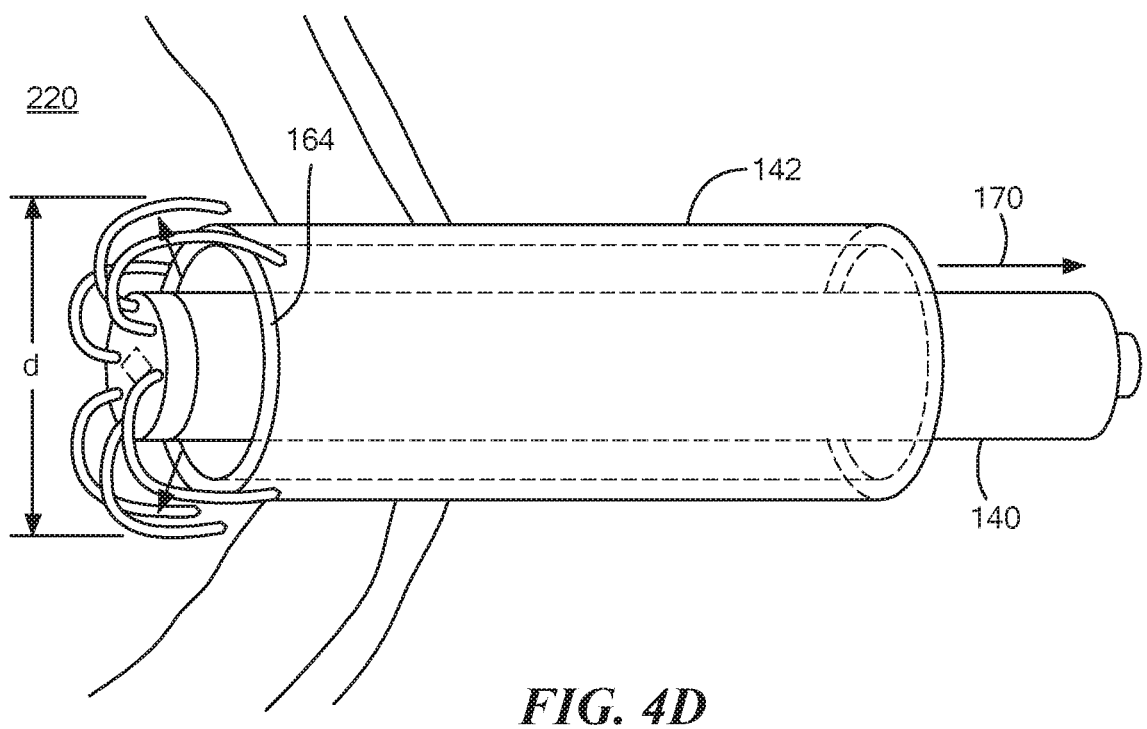
Figure 4E:
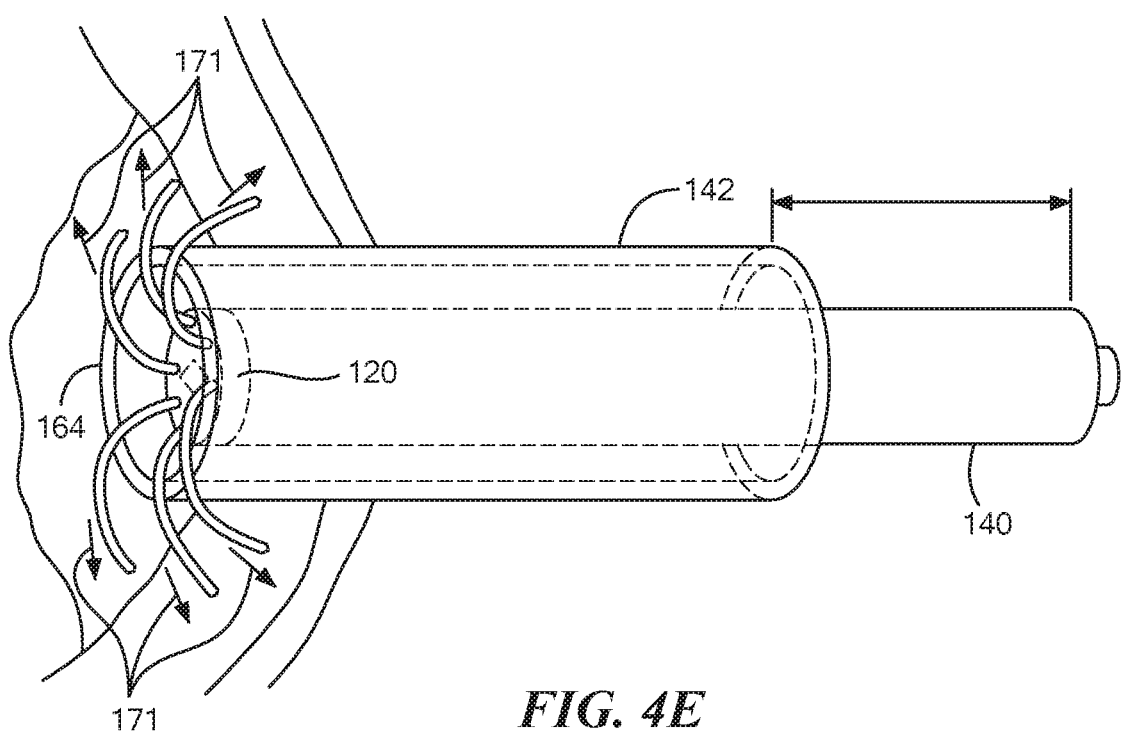

Upon insertion into the stomach lumen 220, the prongs 110 return to an undeformed rest position as they are no longer contracted or "bent" from the inner annular surface 145, achieving an undeformed diameter d, shown in FIG. 4D. It will be noted that the undeformed diameter is greater than the sleeve inside diameter 143. The central hub 120 is responsive to a rearward retraction from the insertion shaft 140, such that the rearward retraction (arrow 170) disposes the surgical tips 117 of each of the plurality of prongs 110 in a radially outward direction, now progressing to FIG. 4E and shown by arrows 171. The outwardly extended, deformed prongs now occupy a larger collective diameter than the undeformed diameter d, as the linkage 130 is configured for retaining the central hub 120 against an annular lip 164 of the insertion sleeve 142 extending the prongs 110 outward and disposing the hub adjacent the closure site 190.

The insertion shaft 140 includes a retention and release mechanism between the central hub 110 and the shaft 140, such that the retention mechanism is configured to retain the clip 100 during partial shaft retraction for engaging the clip against the interior stomach wall. The release mechanism is adapted to disengage the clip by release of the central hub 120 from the shaft 140 following engagement of the prongs in the interior stomach wall, discussed in more detail below in FIGS. 5A and 5B.

Figure 4F:
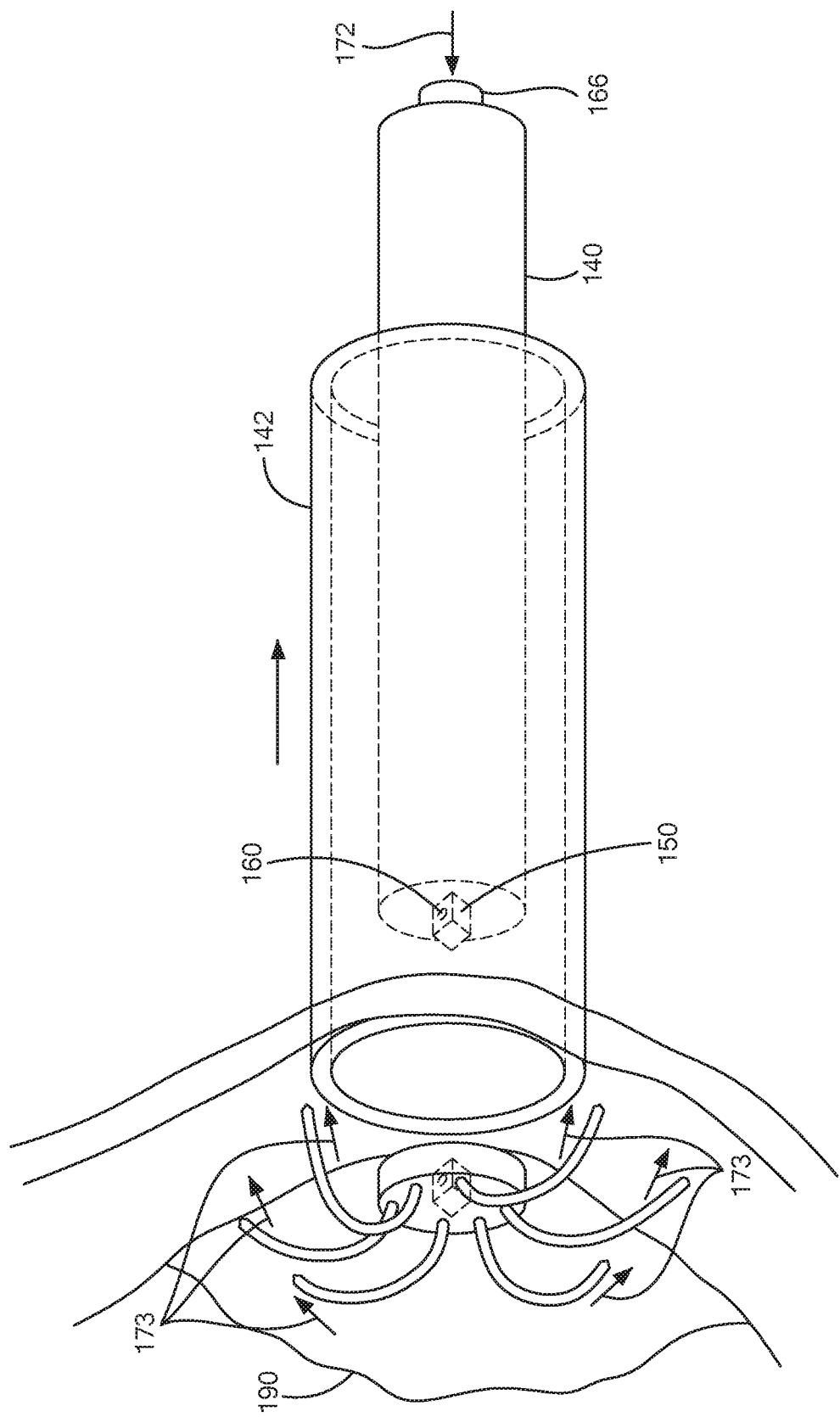

Referring to FIG. 4F, following disposition of the plurality of prongs 110 in the extended position, a release button 166, lever or other actuator activates, show by arrow 172, releasing the linkage 130 such that the distal ends 117 of the prongs 110 are biased towards the central point 122, shown by arrows 173, as the central point is aligned on an axis defined by the sleeve 142 and insertion path of the shaft 140 and therefore locates the prongs centered around the fistula to be closed, while the biased retraction of the surgical tips 117 at the ends of the deformed prongs 110 draws the tissue together for closure and healing.

Figure 5A:
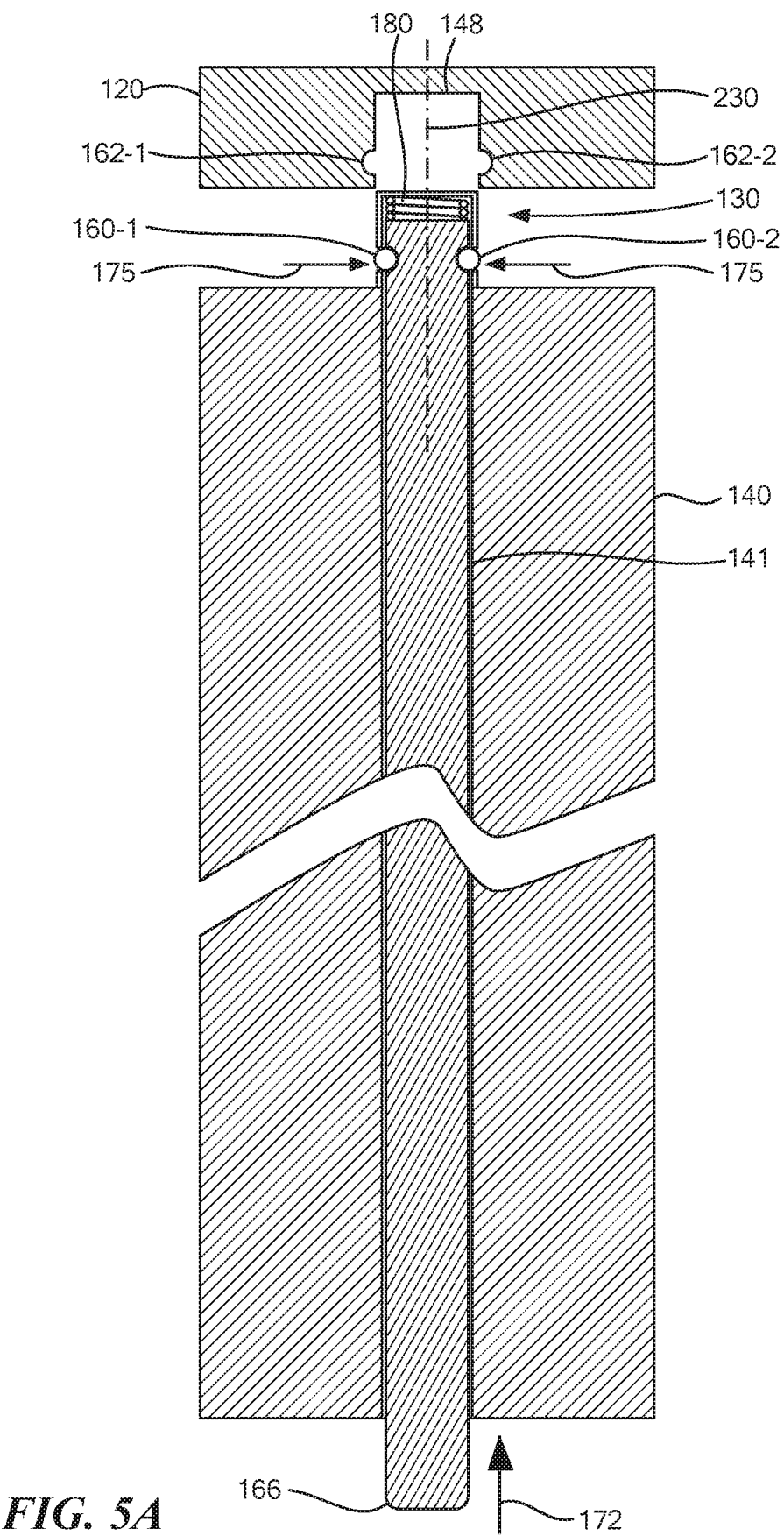
FIGS. 5A-5B show an example configuration of linkage engagement and detachment of the clip of FIGS. 4A-4F.
Figure 5B:
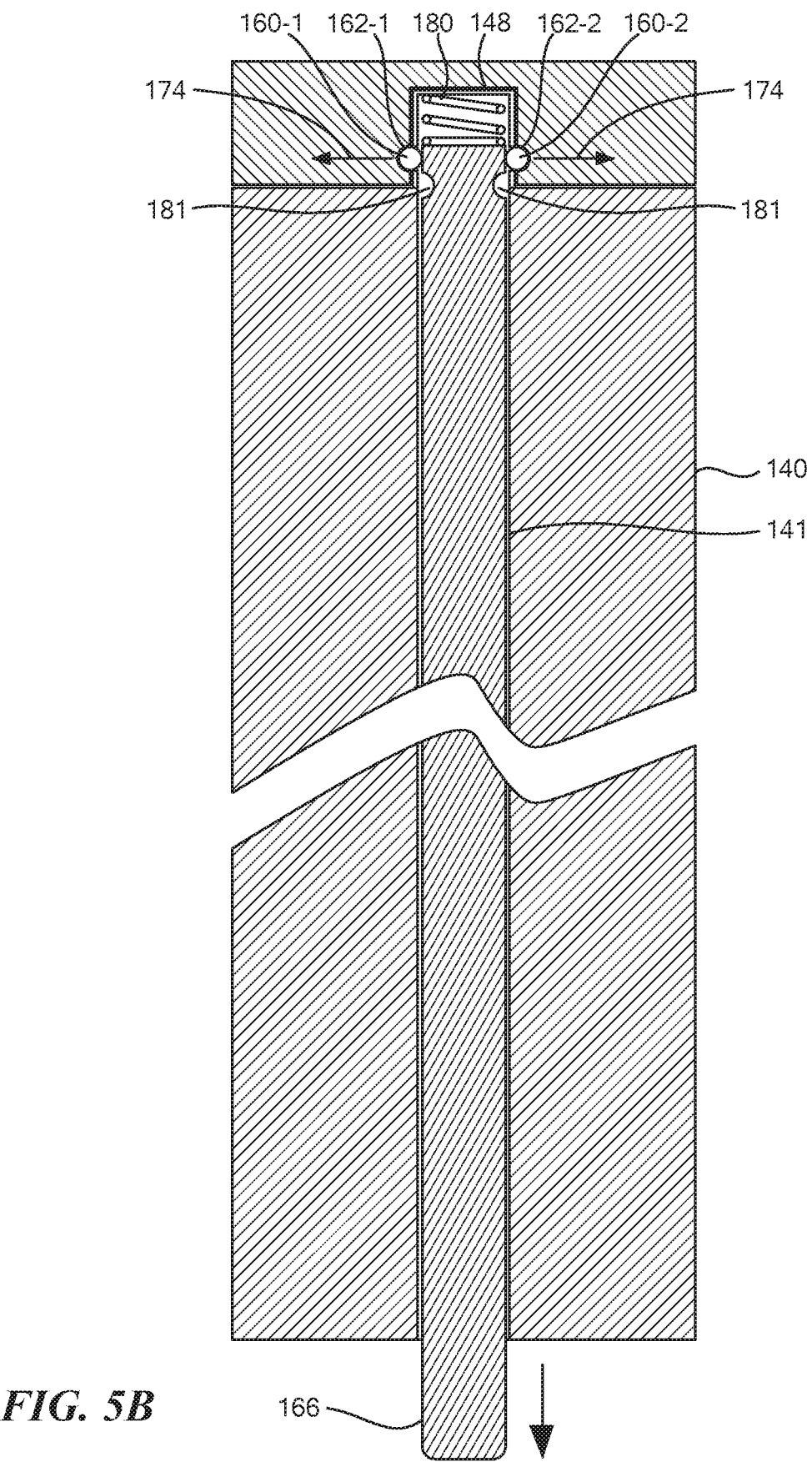

FIGS. 5A-5B show an example configuration of linkage engagement and detachment of the clip of FIGS. 4A-4F. Referring to FIGS. 4A-5B, the method for insertion of a gastrocutaneous clip device includes engaging a central hub 120 of the clip 100 with an insertion tip or appendage 150 on a distal end of the insertion shaft, such that the central hub 120 is retained by a selective linkage responsive to a button 166 on a proximate end of the insertion shaft 140. As shown in FIGS. 4A and 4C, the insertion shaft 140 slideably engages the central hub 120 with the insertion sleeve 142, such that the central hub has a plurality of deformable prongs 110 slideably engaging the inner annular surface 145 of the insertion sleeve 140 for defining a compressed radius of the collective plurality of prongs 110.

The linkage 130 may include any suitable selectively disengageable attachment. In the example of FIGS. 5A and 5B, the linkage 130 includes selectively retractable protrusions 160-1 ... 160-2 (160 generally) such as dimples or ball bearings adapted for engaging a receptacle 162. The protrusions 160 are activated by a plunger 141 extending axially in the insertion shaft 140 for disposing the protrusions laterally in a direction perpendicular to the axis 230 for engaging the receptacle 162-1 ... 162-2 (162 generally). As a tip of the plunger 141 enters the socket 148, the protrusions 160 engage the receptacles 162, and a spring 180 pushes the plunger slightly out of the end of the appendage 150 such that the protrusions are forced out of the recesses 181 and into a locking engagement with the receptacles 162, shown by arrows 174. In an example configuration, the protrusions 160 may be ball bearings or other protrusions responsive to selective retraction.

The insertion sleeve 142 is disposed in a surgical pathway defined by the fistula 210 to a closure site 190 in the lumen 220, shown in FIG. 4B. The central hub 120 is disposed through the insertion sleeve 142 via the insertion shaft 140 from the proximate end, shown in FIG. 4C. The deformable prongs 110 are restored to a rest position from emergence from a distal end of the insertion sleeve 142, as depicted in FIG. 4D, and the plurality of deformable prongs 110 are disposed to an extended position by retracting the central hub 120 via the insertion shaft 140 against the annular lip 164 of the distal end of the insertion sleeve, such that the extended position defines a larger collective radius than the rest position. The linkage 130 secures the central hub 120 to the appendage 150 against a resistive force of the prongs 110, causing the prongs to expand radially.

Once expanded, retraction of the insertion shaft and insertion sleeve is performed concurrently for maintaining the extended position of the plurality of prongs during engagement with the closure site 190. To engage the prongs 110 with the closure site 190, the insertion sleeve 142 is retracted for implantation of the prongs biased for deformable return to the rest position around the closure site 190.

The selective linkage 130 may then be disengaged for retracting the insertion shaft from the central hub 120. The linkage 130 is responsive to a release defined by button 166, such that the release retracts the protrusions 160 for disengagement and/or installation of the central hub 120 and prongs 110 at the closure site 190. The depressed button 166 releases the linkage 130 by allowing the protrusions 160 to retreat into the recesses 181, shown by arrows 175 (FIG. 5A).

Other suitable protrusion 160 and recess 182, and socket 148/appendage 150 arrangements may be envisioned for selectively securing the insertion shaft 140 to the central hub 120 prior to release of the clip 100 at the surgical site 190 for closure. For example, the linkage 130 may include a tether securing the central hub 120 to the insertion shaft, such that the tether is adapted for controlled release following insertion of the central hub 120 and prongs 110.

Figure 6:
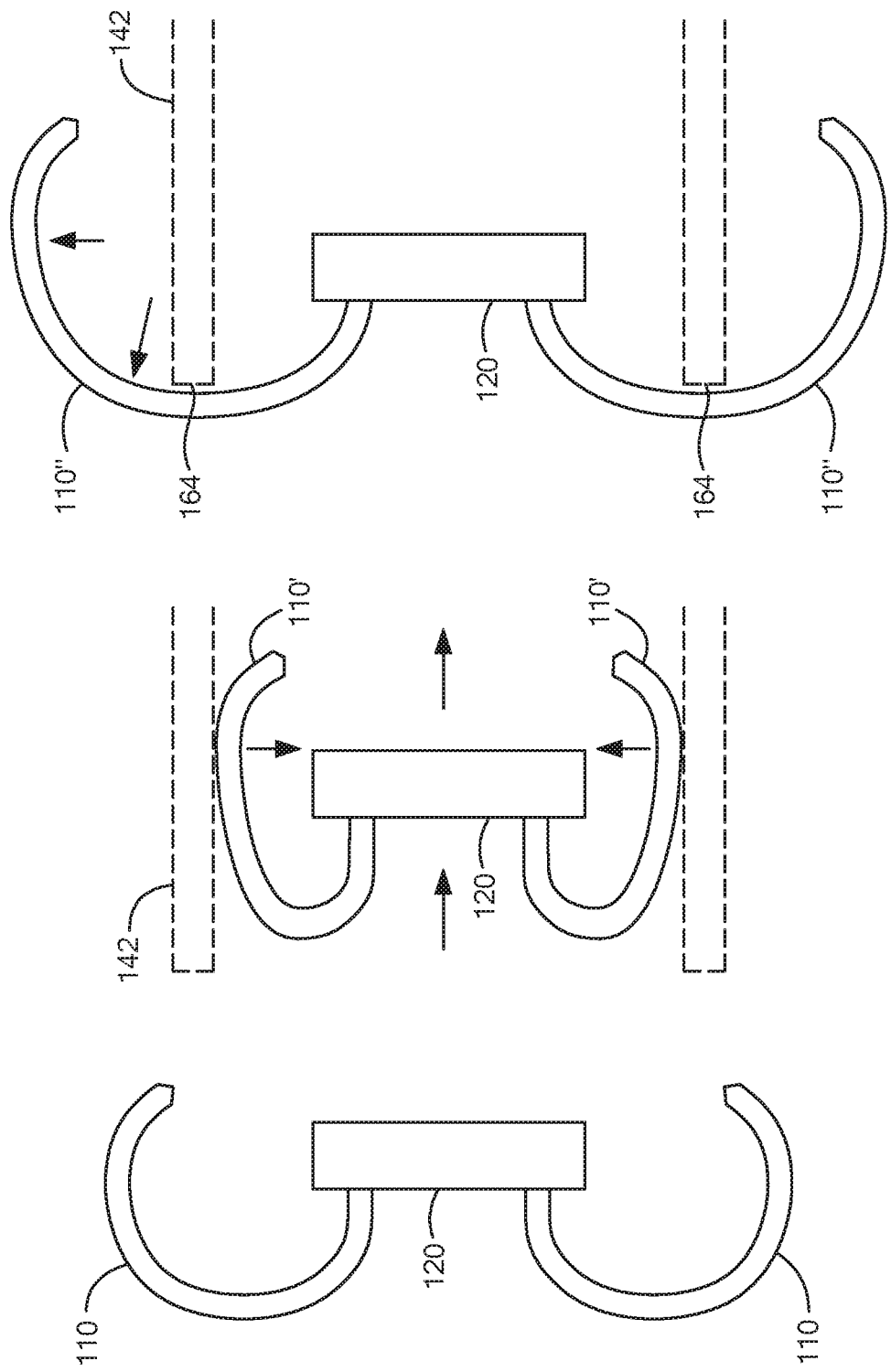
FIG. 6 shows a side view of prong deformation and radii during insertion.

FIG. 6 shows a side view of prong deformation and radii during insertion. Referring to FIG. 6, the clip 100 device has a rest position in an undeformed state defined by undeformed prongs 110, an extended position defined by outwardly extended prongs 110" such that the prongs are biased away from the central point defining the insertion axis or closure site, and a compressed position defined by articulated prongs 110' collectively occupying a smaller diameter area than the rest position. The compressed position 110' results from slideably passing through the insertion sleeve 142, and the expanded position results from the central hub 120 being drawn backwards into the sleeve 142 against lip 164 after the prongs 110 have emerged and returned to rest position 110 on the internal stomach lumen 220 adjacent the site 190.

It follows from FIGS. 4A-6 that the compressed position is defined by the inner diameter 143 of the insertion sleeve 142, such that the insertion sleeve 142 is adapted to slideably receive and deform the plurality of prongs 110 in a radial manner collectively with the other prongs of the plurality of prongs. The extended position defines a radius based on axial retraction of the insertion shaft 142 for disposing the plurality of prongs against the annular lip 164 of the insertion sleeve 142.

Figure 7A:
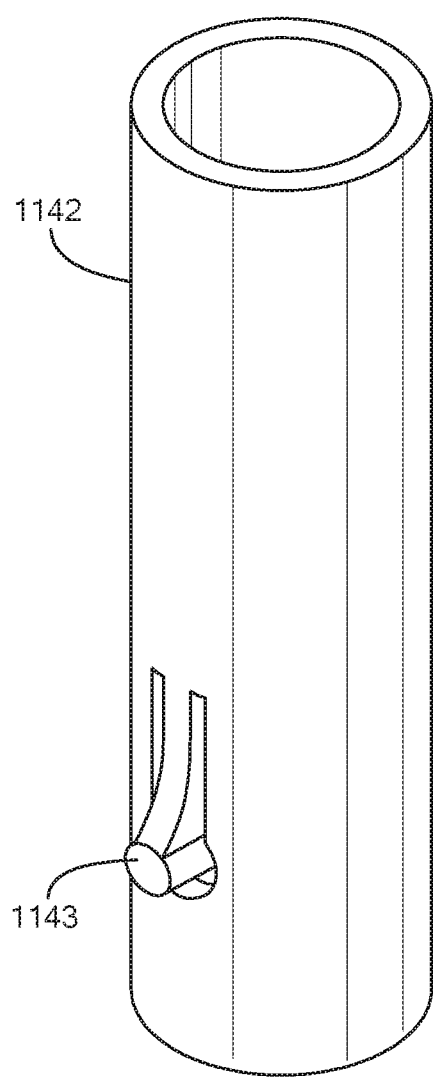
FIGS. 7A-7C show yet a further configuration of the gastrocutaneous clip.
Figure 7B:
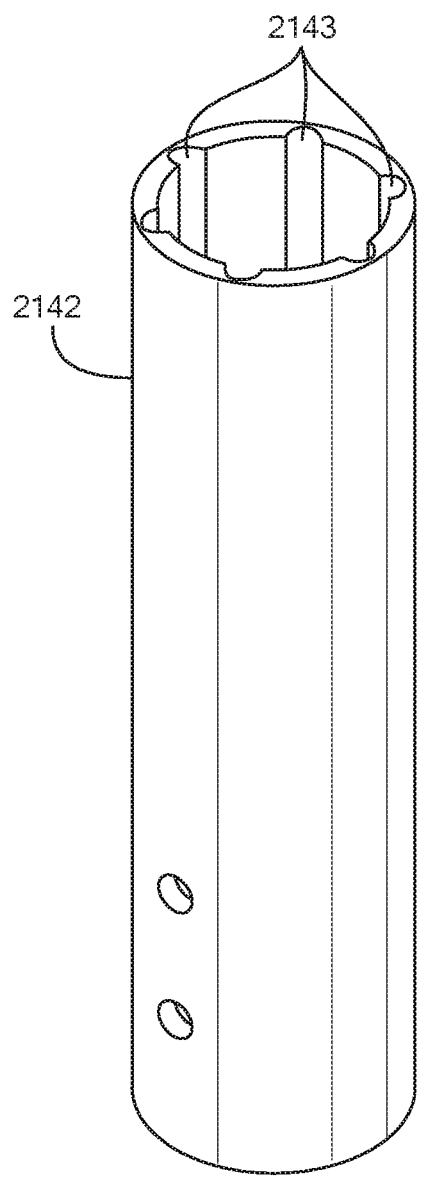
Figure 7C:
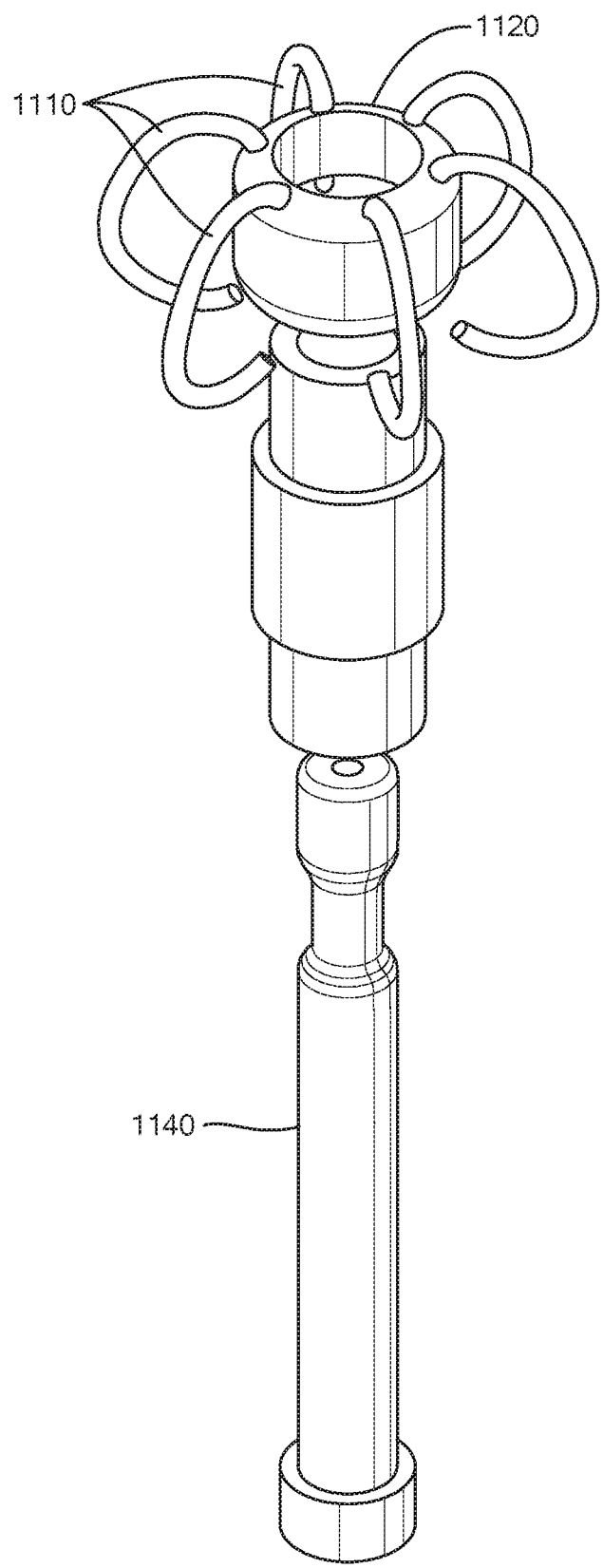

FIGS. 7A-7C show yet a further configuration of the gastrocutaneous clip. A sleeve 1142 include resilient inserts 1143 for assisting insertion depth gauging. A grooved sleeve 2142 includes grooves 2143, to receive a prong 110 as it deforms in the sleeve 142. The inner annular surface of the sleeve 2143 has a plurality of grooves 2143, such that each groove of the plurality of grooves corresponds to a respective one of the prongs 110 for slideable engagement therewith. An alternate shaft 1140 and central hub 1120 has prongs 1110 that emerge from the hub in a slightly more forward position.

Figure 8B:
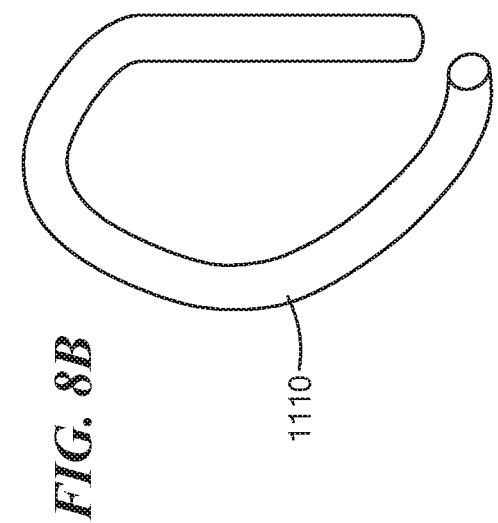
FIGS. 8A-8C show an alternate prong shape to the configurations of FIGS. 1A-6.
Figure 8A:
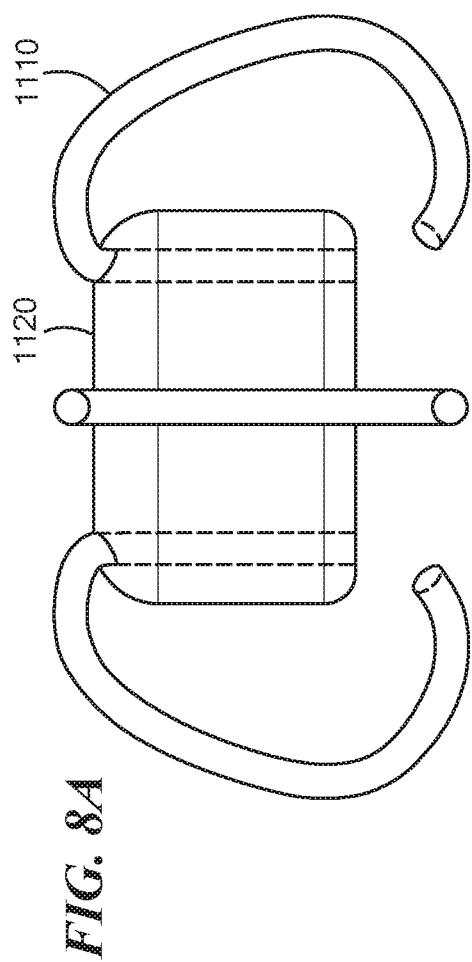
Figure 8C:
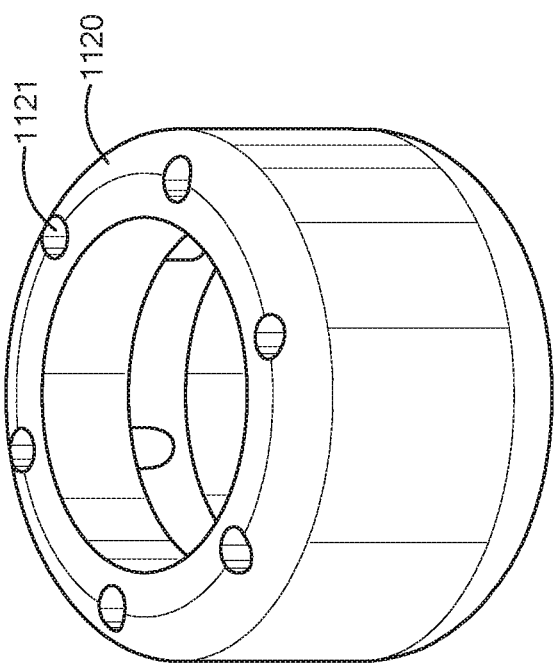

FIGS. 8A-8C show an alternate prong shape to the configurations of FIGS. 1A-6 In a typical arrangement, the clip 100 has between 4 and 6 prongs and is adapted to radially compress to a compressed diameter for sleeve insertion and radially expand to an expanded diameter for engaging the interior stomach wall prior to fistula closure, as described above with respect to FIG. 6, The shape of the prong may be any deformable, inverted shape that biases for fistula closure from the central hub 120, and may have the appearance of an arc, semicircle, "U", "D" or a combination of these. FIG. 8A shows a side schematic view of the alternate central hub 1120 and prong 1110. FIGS. 8B and 8C show perspective views of the prong 1110 and central hub 1120 including forward facing receptacles 1121 for receiving the proximate end of the prongs 1110. Generally, the prongs 110 of the clip 100 are formed from a biocompatible or biodegradable material including nitinol, along with the central hub.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A gastrocutaneous clip device comprising:
    a plurality of prongs defined by a deformable material, the prongs extending radially from a forward side of a central hub in an inverted shape, the inverted shape of each of the plurality of prongs converging towards a central point at a distal end,
    a linkage on a rearward side of the central hub, the linkage adapted for selectively engaging an insertion shaft for insertion and release of the central hub;
    the prongs extending in a lateral or forward direction from the central hub, the forward direction opposed from the rearward side, and inverting towards facing a rearward direction defined by the rearward side at the distal end; and
    a surgical tip at the distal end of each prong of the plurality of prongs, the surgical tip adapted for engaging a surgical region,
    each prong adapted to deformably articulate for disposing the plurality of prongs in a radial arrangement around a closure site.

2. The device of claim 1 wherein the plurality of prongs are adapted to slideably engage an inner annular surface of an insertion sleeve, the inner annular surface having a diameter based on a compressed articulation of each prong of the plurality of prongs as the central hub disposes axially through the tube for insertion.

3. The device of claim 1 wherein the linkage is responsive to a release, the release retracting the protrusions for disengagement and installation of the central hub and prongs at the closure site.

4. The device of claim 3 wherein the central hub is responsive to a rearward retraction from an insertion shaft, the rearward retraction disposing the surgical tips of each of the plurality of prongs in a radially outward direction, the linkage configured for retaining the central hub against an annular lip of an insertion sleeve disposing the hub adjacent the closure site.

5. The device of claim 1 wherein the linkage includes selectively retractable protrusions adapted for engaging a receptacle, the protrusions activated by a plunger extending axially in the insertion shaft for disposing the protrusions laterally in a direction perpendicular to the axis for engaging the receptacle.

6. The device of claim 5 wherein the device has a rest position in an undeformed state defined by undeformed prongs, an extended position defined by outwardly extended prongs such that the prongs are biased away from the central point, and a compressed position defined by articulated prongs collectively occupying a smaller diameter area than the rest position.

7. The device of claim 6 wherein the compressed position is defined by an inner diameter of an insertion sleeve, the insertion sleeve adapted to slideably receive and deform the plurality of prongs in a radial manner collectively with the other prongs of the plurality of prongs.

8. The device of claim 6 wherein the extended position defines a radius based on axial retraction of the insertion shaft for disposing the plurality of prongs against an annular lip of the insertion sleeve.

9. The device of claim 8 wherein following disposition of the plurality of prongs in the extended position, the distal ends of the prongs are biased towards the central point, the central point aligned on an axis defined by the sleeve and insertion path of the shaft.

10. The device of claim 1 wherein the linkage includes a square, circular or polygonal insertion tip on one of the insertion shaft and the central hub, and a corresponding tip receptacle on the other of the insertion shaft and the central hub, and at least one protrusion extending perpendicularly from an axis defined by an elongated direction of the insertion shaft.

11. The device of claim 1 wherein the linkage includes a tether securing the central hub to the insertion shaft, the tether adapted for controlled release following insertion of the central hub and prongs.

12. The device of claim 2 wherein the inner annular surface of the sleeve has a plurality of grooves, each groove of the plurality of grooves corresponding to a respective one of the prongs for slideable engagement therewith.

13. A method for insertion of a gastrocutaneous clip device, comprising: engaging a central hub of a clip with a plurality of prongs defined by a deformable material, the prongs extending radially from a forward side of the central hub in an inverted shape, the inverted shape of each of the plurality of props converging towards a central point at a distal end the prongs extending in a lateral or forward direction from the central hub, the forward direction opposed from the rearward side, and inverting towards facing a rearward direction defined by the rearward side at the distal end, and an insertion tip on a distal end of an insertion shaft, the central hub retained by a selective linkage responsive to a button on a proximate end of the insertion shaft; slideably engaging the central hub with an insertion sleeve, the central hub having a plurality of deformable prongs slideably engaging an inner annular surface of the insertion sleeve for defining a compressed radius of the collective plurality of prongs; disposing the insertion sleeve in a surgical pathway to a closure site; disposing the central hub through the insertion sleeve by disposing the insertion shaft from the proximate end; restoring the plurality of deformable prongs to a rest position from emergence from a distal end of the insertion sleeve; disposing the plurality of deformable prongs to an extended position by retracting the central hub via the insertion shaft against an annular lip of the distal end of the insertion sleeve, the extended position defining a larger collective radius than the rest position; retracting the insertion shaft and insertion sleeve concurrently for maintaining the extended position of the plurality of prongs during engagement with a closure site; retracting the insertion sleeve for implantation of the prongs biased for deformable return to the rest position around the closure site; and disengaging the selective linkage for retracting the insertion shaft from the central hub.

14. A gastrocutaneous closure device comprising:
a clip having a plurality of prongs defined by a deformable material, the prongs extending radially from a central hub in an arcuate shape, the arcuate shape of each of the plurality of prongs converging towards a central point at a distal end, the proximate end of the prongs extending from the central hub;
an elongated shaft adapted to selectively engage the central hub, the elongated shaft having a length based on a gastric tract resulting from a gastrostomy tube removal; and
a sleeve having a diameter for insertion into a surgical tract defining a gastrocutaneous fistula for the gastrostomy tube, an inside diameter of the sleeve adapted for passage of the shaft,
the clip adapted to:
radially compress for passage through the sleeve for insertion into a stomach lumen;
radially expand in response to partial retraction of the shaft through the sleeve; and
radially compress against an interior stomach wall for engaging the prongs against the stomach wall and drawing the stomach wall inward toward the hub for closing the fistula.

15. The device of claim 14 wherein the clip has between 4 and 6 prongs and is adapted to radially compress to a compressed diameter for sleeve insertion and radially expand to an expanded diameter for engaging the interior stomach wall prior to fistula closure.

16. The device of claim 14 wherein the sleeve is configured to retain a cauterization substance for deposition or release around the gastrocutaneous fistula during insertion.

17. The device of claim 14 further comprising a retention mechanism between the hub and the shaft, the retention mechanism configured to retain the clip during partial shaft retraction for engaging the clip against the interior stomach wall.

18. The device of claim 17 further comprising a release mechanism adapted to disengage the clip by release of the hub from the shaft following engagement of the prongs in the interior stomach wall.

19. The device of claim 16 wherein the cauterization substance is silver nitrate.

20. The device of claim 1 wherein the clip is formed from a biocompatible or biodegradable material including nitinol.

* * * * *